United States Patent [19]

Case et al.

[11] 4,052,405

[45] Oct. 4, 1977

[54] MANUFACTURE OF 1,1'-DIALKYL-4,4'-BIPYRIDYLIUM SALTS

[75] Inventors: John Reginald Case; Geoffrey James Moore, both of Runcorn, England

[73] Assignee: Imperial Chemical Industries Limited, London, England

[21] Appl. No.: 357,656

[22] Filed: May 7, 1973

[30] Foreign Application Priority Data

Sept. 4, 1972 United Kingdom .............. 40953/72

[51] Int. Cl.$^2$ ........................................... C07D 213/22
[52] U.S. Cl. ........................ 260/294.8 R; 260/296 D
[58] Field of Search ..................... 260/296 D, 294.8 R

[56] References Cited

U.S. PATENT DOCUMENTS

| 3,332,959 | 7/1967 | Braunholtz .................. | 260/294.8 R |
| 3,413,111 | 11/1968 | Braunholtz et al. ......... | 260/294.8 R |

FOREIGN PATENT DOCUMENTS 1,390,773   1/1965   France .............................. 260/296 D

OTHER PUBLICATIONS

Groggins, Unit Processes in Organic Synthesis, Third Edition, McGraw-Hill, pp. 1947, 567.
Groggins I – Unit Processes in Organic Synthesis, p. 822 (4th Edition, McGraw-Hill Book Co., Inc., New York (1952).
Kirk-Othmer – Encyclopedia of Chemical Technology, John Wiley & Sons, Inc., New York, vol. 16, pp. 859, 863 (1968); vol. 19, p. 486 (1969).

Primary Examiner—Alan L. Rotman
Attorney, Agent, or Firm—Cushman, Darby & Cushman

[57] ABSTRACT

A 1,1'-dialkyl-4,4'-bipyridylium salt is prepared from the corresponding 4,4'-bipyridyl using an alkylsulphate salt as the quaternizing agent.

2 Claims, No Drawings

MANUFACTURE OF 1,1'-DIALKYL-4,4'-BIPYRIDYLIUM SALTS

BACKGROUND OF THE INVENTION

This invention relates to the manufacture of 1,1'-dialkyl-4,4'-bipyridylium salts.

It is known that dialkylsulphates, for example dimethylsulphate, may be used as quaternising agents in the preparation of 4,4'-bipyridylium salts from 4,4'-bipyridyls. In the known reaction it is usual to employ at least the stoichiometric proportion of the dialkylsulphate for the formation of the alkylsulphate salt, for example in the formation of the dimethosulphate:

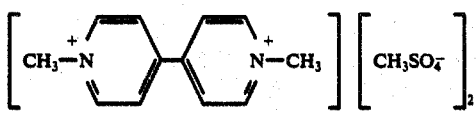

from 4,4'-bipyridyl itself, at least 2 moles of dimethylsulphate are used per mole of 4,4'-bipyridyl.

The aforesaid reaction has the disadvantage that only up to half of the alkyl groups in the dialkylsulphate are utilised in the production of the 1,1'-dialkyl-4,4'-bipyridylium cation. Furthermore, dialkylsulphates are highly reactive reagents which are unpleasant, and potentially dangerous, to handle in the quaternisation process.

SUMMARY OF THE INVENTION

It is an object of the present invention to avoid the necessity of using a dialkylsulphate as quaternising agent while obtaining high efficiency of conversion of the 4,4'-bipyridyl and high efficiency of utilisation of the alkyl groups of the quaternising agent.

According to the present invention a 1,1'-dialkyl-4,4'-bipyridylium salt is prepared from a 4,4'-bipyridyl using an alkylsulphate salt as quaternising agent.

The use of an alkylsulphate salt in the quaternisation process leads to greater efficiency in the utilisation of the alkyl groups since a bipyridylium salt can be obtained without the wasteful incorporation of one alkyl group in the anion for each alkyl group introduced into the cation.

DETAILED DESCRIPTION OF THE INVENTION

It is preferred to use a salt of an alkylsulphuric acid containing up to 4 carbon atoms in the alkyl group. Salts of methylsulphuric acid are especially preferred.

When a metal salt is used, this is preferably an alkali-metal salt, for example a sodium salt; thus, for example, sodium methosulphate ($NaCH_3SO_4$) may conveniently be used.

The alkylsulphate may be a 1,1'-disubstituted-4,4'-bipyridylium di(alkylsulphate), for example 1,1'-dimethyl-4,4'-bipyridylium di(methosulphate). In this embodiment of the invention a 1,1'-dialkyl-4,4'-bipyridylium di(alkylsulphate) may be prepared in a preliminary stage by the known method of interacting a 4,4'-bipyridyl with a dialkylsulphate; the use of the 1,1'-dialkyl-4,4'-bipyridylium di(alkylsulphate) thus prepared as the quaternising agent in the process of the present invention, while not avoiding the use of a dialkylsulphate in the preliminary stage, increases the overall efficiency of utilisation of the alkyl groups of the dialkylsulphate.

The alkylsulphate salt used as the quaternising agent may, if desired, be introduced as a solid into the reaction medium, which may comprise for example water and/or an alcohol. It is an advantage of the present invention, however, that the quaternisation may readily be carried out in an aqueous medium. Thus the alkylsulphate salt may be prepared in the form of an aqueous solution which is used directly in the quaternisation process. For example, an aqueous solution of an alkali-metal alkylsulphate may be prepared by first preparing an alkylsulphuric acid from sulphuric acid and the appropriate alcohol and neutralising the alkyl-sulphuric acid thus obtained with an aqueous solution of the appropriate base (for example an alkali-metal hydroxide).

It is preferred to use at least 2 moles of alkylsulphate per mole of the 4,4'-bipyridyl (i.e. at least the stoichiometric proportion required for the formation of the 1,1'-dialkyl-4,4'-bipyridylium cation). The reaction with an alkylsulphate is preferably carried out at a temperature of at least 60° C, for example in the range 75° C to 250° C. The reaction is conveniently carried out at the boiling point of the reaction mixture (for example under reflux conditions).

While the process is especially applicable to the quaternisation of 4,4'-bipyridyl itself, quaternary salts of substituted 4,4'-bipyridyls may also be prepared by the process described herein, including salts of 4,4'-bipyridyls substituted in one or both of the pyridine nuclei with one or more alkyl groups, especially one or more alkyl groups having 1 to 4 carbon atoms (for example 2,2'-dimethyl-4,4'-bipyridyl and 2,6'-dimethyl-4,4'-bipyridyl).

It is believed than at least some of the 1,1'-dialkyl-4,4'-bipyridylium cations in the product are associated with sulphate ions, but the nature of the anions may depend to some extent upon the conditions used in the quaternisation process, especially upon the acidity and/or the water content of the reaction medium.

If desired, the 1,1'-di-alkyl-4,4'-bipyridylium salt may be separated from the reaction products by known methods. In general, however, the bipyridylium salts are obtained in a form which requires little treatment before they are suitable for use as herbicides. Thus in many cases the product mixture may require no more than some dilution with water (and possibly adjustment of pH) before it is ready for application. Other ingredients, for example corrosion inhibitors and surface-active agents may also be incorporated in the solution if desired.

The invention is illustrated by the following Examples.

EXAMPLE 1

A mixture of 4,4'-bipyridyl (0.024 mole), 1,1'-dimethyl-4,4'-bipyridylium dimethosulphate (0.024 mole) and water (70 ml) was heated under conditions of reflux at the boiling point of the reaction mixture (about 100° C) for 36 hours. The reaction mixture was the cooled and analysed colorimetrically and polarographically.

The reaction product was found to contain 1,1'-dimethyl-4,4'-bipyridylium cation in an amount (0.035 mole) corresponding to a 44% conversion of the 4,4'-bipyridyl used and 1-methyl-4(4-pyridyl) pyridinium cation in an amount (0.007 mole) corresponding to a 29% conversion of the 4,4'-bipyridyl used.

EXAMPLE 2

A mixture of 4,4'-bipyridyl (1.56g, 0.01 mole), sodium methosulphate (2.68g, 0.02 mole), and water (30 ml) was heated under conditions of reflux at the boiling point of the reaction mixture (about 100° C) for 24 hours. The reaction mixture was then cooled and analysed colorimetrically and polarographically.

The conversion of 4,4'-bipyridyl into 1,1'-dimethyl-4,4'-bipyridylium ion was 45% and the conversion into 1-methyl-4(4-pyridyl) pyridinium ion was 47%.

EXAMPLE 3

A mixture of 4,4'-bipyridyl (0.024 mole), 1,1'-dimethyl-4,4'-bipyridylium dimethosulphate (0.024 mole) and water (70 ml) was sealed in a 125 ml autoclave and heated under autogeneous pressure at 150° C for 5 hours. The reaction product was washed out with a little water and analysed colorimetrically and polarographically.

The reaction product was found to contain 1,1'-dimethyl-4,4'-bipyridylium cation in an amount (0.037 mole) corresponding to a 54% conversion of the 4,4'-bipyridyl used and 1-methyl-4(4-pyridyl) pyridinium cation in an amount (0.009 mole) corresponding to a 38% conversion of the 4,4'-bipyridyl used.

EXAMPLE 4

A mixture of 4,4'-bipyridyl (1.56g, 0.01 mole), sodium methosulphate (2.68g, 0.02 mole) and water (50 ml) was sealed in a 100 ml autoclave and heated under autogeneous pressure at 150° C for 5 hours. The reaction product was washed out with a little water and analysed colorimetrically and polarographically.

The conversion of 4,4'-bipyridyl into 1,1'-dimethyl-4,4'-bipyridylium ion was 54% and the conversion into 1-methyl-4(4-pyridyl) pyridinium ion was 43%.

EXAMPLE 5

A mixture of 4,4'-bipyridyl (1.56g, 0.01 mole), sodium methosulphate (3.35g, 0.025 mole), and water (50 ml) was sealed in a 100 ml autoclave and heated under autogeneous pressure at 150° C for 5 hours. The reaction product was washed out with a little water and analysed colorimetrically and polarographically.

The conversion of 4,4'-bipyridyl into 1,1'-dimethyl-4,4'-bipyridylium ion was 67% and the conversion into 1-methyl-4(4-pyridyl) pyridinium ion was 26%.

EXAMPLE 6

A mixture of 4,4'-bipyridyl (1.56g, 0.01 mole), sodium methosulphate (4.02g, 0.03 mole), and water (50 ml) was sealed in a 100 ml autoclave and heated under autogeneous pressure at 150° C for 5 hours. The reaction product was washed out with a little water and analysed colorimetrically and polarographically.

The conversion of 4,4'-bipyridyl into 1,1'-dimethyl-4,4'-bipyridylium ion was 85% and the conversion into 1-methyl-4(4-pyridyl) pyridinium ion was 14%.

EXAMPLE 7

A mixture of 2,2'-dimethyl-4,4'-bipyridyl (1.84g, 0.01 mole) sodium methosulphate (4.02g, 0.03 mole) and water (30 ml) was heated under conditions of reflux at the boiling point of the reaction mixture (about 100° C) for 48 hours. The reaction product was cooled, diluted with water, and analysed colorimetrically for 1,1',2,2'-tetramethyl-4,4'-bipyridylium ion. The element of 1,1',2,2'-tetramethyl-4,4'-bipyridylium ion found was 0.90g, representing a 42% conversion of 2,2'-dimethyl-4,4'-bipyridyl into the diquaternary salt.

EXAMPLE 8

A mixture of 4,4'-bipyridyl (1.56g, 0.01 mole), sodium ethylsulphate (4.44g, 0.03 mole) and water (30 ml) was heated under conditions of reflux at the boiling point of the reaction mixture (about 100° C) for 48 hours. The reaction product was cooled, diluted with water and analysed colorimetrically. The amount of 1,1'-diethyl-4,4'-bipyridylium ion found was 1.09g, representing a 51% conversion of 4,4'-bipyridyl into the diquaternary salt.

We claim:

1. A method of preparing a 1,1'-dialkyl-4,4'-bipyridylium salt which comprises interacting a 4,4'-bipyridyl with a quaternizing agent consisting essentially of a 1,1'-disubstituted-4,4'-bipyridylium di(alkylsulphate).

2. A method according to claim 1 wherein the alkylsulphate is 1,1'-dimethyl-4,4'-bipyridylium di(methosulphate).

* * * * *